United States Patent [19]

Holder et al.

[11] Patent Number: 4,837,016

[45] Date of Patent: Jun. 6, 1989

[54] PROTOZOAL ANTIGEN

[75] Inventors: Anthony A. Holder, Biggin Hill; Robert R. Freeman, London, both of England

[73] Assignee: Burroughs Wellcome Co., Research Triangle Park, N.C.

[21] Appl. No.: 891,055

[22] Filed: Jul. 31, 1986

Related U.S. Application Data

[63] Continuation of Ser. No. 660,563, Oct. 16, 1984, abandoned, which is a continuation of Ser. No. 379,942, May 19, 1982, abandoned.

[30] Foreign Application Priority Data

May 21, 1981 [GB] United Kingdom ............... 8115555
Aug. 3, 1981 [GB] United Kingdom ............... 8123709

[51] Int. Cl.$^4$ .................. A61K 39/015; C12N 5/00; C07K 15/04
[52] U.S. Cl. ............................ 424/88; 530/350; 530/412; 530/413; 435/68; 435/240.26
[58] Field of Search ............... 424/88; 435/240.26, 435/68; 530/412, 413, 350

[56] References Cited

PUBLICATIONS

Kilejian, A., J. Exp. Med., vol. 151, pp. 1534–1538, 1980.
Kilejian, A., Proc. Natl. Acad. Sci., vol. 77, pp. 3695–3699, 1980.
Chemical Abstracts, vol. 93, p. 675, Abst. No. 43548x, 1980.
Chemical Abstracts, vol. 93, p. 676, Abst. No. 43561, 1980.
Penin, L. H., et al., Nature, vol. 289, pp. 301–303, 1981.
Freeman et al., Host. Invader Interplay, Ed. H. Van den Bosche, Elsaveir, North Holland, Biomedical Press, pp. 121–124, 1980.
Freeman et al., Experimental Parasitology, vol. 52, pp. 18–24, 1981.

*Primary Examiner*—Blondel Hazel
*Attorney, Agent, or Firm*—Donald Brown

[57] ABSTRACT

Protection inducing antigens or parasites of the genus Plasmodium are described. The antigens have an apparent molecular weight of 1.8 to $2.5 \times 10^5$ and are associated with the membranes of the erythrocytic schizont forms of the parasite. The antigens may be incorporated into vaccines and used for the inducing of immunity into susceptible vetebrate hosts including humans. Methods for the preparation of the antigens are also described.

10 Claims, 1 Drawing Sheet

PROTOZOAL ANTIGEN

This application is a continuation of application Ser. No. 660,563, filed Oct. 16, 1984 now abandoned which is a continuation of application Ser. No. 379,942, filed May 19, 1982 now abandoned.

The present invention relates to antigenic material, to vaccines containing it and to the use thereof to provide immunity to malaria.

The malaria parasites are protozoa belonging to the genus Plasmodium. Part of their complex life cycle involves cyclic asexual replication within the erythrocytes of the vertebrate host, giving rise to the symptoms of the disease known as malaria. The vertebrate host may, in turn, exhibit a protective immune response which is effective against the blood-borne parasites. It is implied, therefore, that the blood forms synthesize antigens which elicit the production of specific, protective antibodies in the infected or immunized host.

During the asexual erythrocytic cycle of replication, free parasites (merozoites) recognize and attach specifically to the surface of erythrocytes, and then invade them by invagination of the plasma membrane. The infected erythrocyte is known as the trophozoite. During the intracellular differentiation of the parasite the nuclear undergoes repeated divisions, to form the schizont. Nuclear division is followed by segmentation of the cytoplasm to form a number of uninucleate intraerythrocytic merozoites. Upon lysis of the schizont membranes, the merozoites are released into the plasma and may attach to, and invade, fresh host erythrocytes.

Immunity to malaria is believed to be mediated by antibodies specific for parasite antigens associated with the schizont and/or merozoite forms of the parasite (see for example Cohen, Proc. R. Soc. London B, 1978, 203; 323–345; Freeman and Parish, Exp. Parasitol, 1981, 51, 18–24).

A number of parasite antigens associated with the schizont membrane have been detected by crossed immunoelectrophoresis of solubilised schizont material against hyperimmune serum (see for example Deans, Dennis and Cohen, Parasitology, 1978, 77 333–344; Schmidt-Ullrich, Wallach and Lightholder, J. exp. Med. 1979, 150, 86–99). In particular the latter group have detected 3 antigens from *Plasmodium knowlesi* schizont membrane of molecular weight 65,000, 90,000 and 125,000. These antigens are precipitated by *P. knowlesi* and *P. falciparum* immune serum. The available data on *P. knowlesi* and *P. falciparum* do not allow definite conclusions as to the developmental stage(s) at which parasite specific antigens are immunogenic or whether the antigens detected are the ones involved in protective immunity (Schmidt-Ullrich et. al "The Host-Invader Interplay", 1980, H. Van den Bossche ed., Elsevier/North Holland, Amsterdam, 117-120).

Schizont antigens of *P. falciparum* have also been described (Kilejian, Proc. Nat. Acad. Sci. 1980, 77, 3695–3699; J. exp. Med., 1980, 151, 1534–1538; Perrin et. al. Trans. Roy, Soc. Trop. Med. Hyg. 1981, 75, 163–165). None of these antigens have been purified or shown to be protective antigens.

Antigens derived from schizont membranes and having molecular weights of up to 200,000 have also been referred to in the literature (Freeman et. al The Host-Invader Interplay, H. Van den Bossche, Ed., Elsevier/-North Holland Biochemical Press 1980, 121-124) but the only antibody described, a monoclonal antibody specific for these antigens was shown not to provide passive immunity.

We have now suprisingly found that an antigen recognised by the aforementioned antibody and originating from a schizont membrane is capable of generating protection against malaria and such an antigen associated with schizont forms of Plasmodium parasites has now been isolated and defined.

The antigen so identified is a protection-inducting proteinaceous antigen of parasites of the genus Plasmodium having the following characteristics:

(i) a molecular weight in the range of $1.8 \times 10^5$ to $2.5 \times 10^5$;

(ii) associated with the membranes of the erythrocytic schizont form of the parasite; and merozoite forms of the parasites; and (iii) is processed intraerythrocytically to discrete fragments possessing the same antigenic properties, and in which the antigen, or the discrete fragments thereof, are associated with the surface membrane of the merozite form of the parasite, and functional derivatives thereof.

These antigenic proteins are known to occur in a number of murine malaria protozoa such as *Plasmodium yoelii*, *P. berghei* and *P. vinckei* spp. and in primate malaria parasites, in particular *P. falciparum*.

By "molecular weight" is meant the apparent molecular weight as determined by polyacrylamide gel electrophoresis and standard molecular weight markers. The molecular weight of the antigenic proteins of the invention may thus be conveniently determined by the techniques described by U. K. Laemmli, Nature, 1970, 227, 680–685. Convenient standard molecular weight markers include, for example, spectrin heterodimer ($2.2 \times 10^5$ molecular weight and $2.4 \times 10^5$ molecular weight).

The term 'associated' as used herein refers not only to proteinaceous antigenic material originating from the schizont or merozoite forms of malaria parasites but to antigenically identical material of similar or identical amino acid sequence deriving from any other source.

The antigens of the present invention are synthesized only during the later stages of the parasite's intracellular development. Thus for *P. falciparum* the onset of synthesis of this antigen co-incides with the start of schizogeny and continues right through until the end of the intracellular stage.

It has been found that a characteristic of the parent antigen is that, no matter the parasite from which it derives, it is processed intraerythrocytically to discreet fragments of lower molecular weight which possess the same antigenic properties. The molecular weight of these fragments varies with that of the particular parent antigen but it has been found that the major fragments have molecular weights which are respectively $0.3–0.4 \times 10^5$; $0.7–0.8 \times 10^5$; $1.0–1.4 \times 10^4$ lower than that of the parent antigen.

In synchronised cultures of *P. falciparum* the processing is not a co-translational event, but appears to co-incide with merozoite maturation or release, at the end of the intraerthrocytic development cycle. It is likely that discrete fragment(s) rather than the antigen itself are on the surface of merozoites.

It will be appreciated by one skilled in the art that the benefit of the immunogenic properties of the antigens defined above will be obtained not only from the parent antigens themselves but also from immunogenic fragments thereof, including those generated intraerythrocytically, and materials incorporating the parent antigens or fragments thereof. All such materials are referred to herein as "functional dervatives".

The antigenic proteins may be prepared by any method known in the art for the preparation of such antigens. All such methods comprise either isolation of the antigenic protein from the parasite or chemically or biologically reproducing the antigenic protein.

In one such method the antigenic proteins may be isolated from the schizont forms of the parasite by means of monoclonal antibodies specific for the antigens of the invention. The technique of antigen separation by means of monoclonal antibodies has not previously been applied to the purification of malaria antigens.

There is thus provided a method for the preparation of an antigenic protein as defined herein which comprises the steps of:

(i) solubilising erythrocytes containing the schizont forms of a Plasmodium parasite;

(ii) contacting the solubilised material with a monoclonal antibody specific for the desired antigenic protein to provide an antibody antigen complex; and (iii) recovering the antigenic protein from the antibody-antigen complex.

There is also provided an antigenic protein as defined herein when prepared by the above defined method. The schizonts may be solubilised by any method known in the art for effecting such solubilisation. Suitable conditions which solubilise parasite material without extensive proteolysis and denaturation are employed. In particular they may be solubilised by contacting them with a detergent, which may be of the ionic or non-ionic type although non-ionic detergents are preferred. Examples of such detergents include Nonidet P40, Triton X-100, Brij 99 (Registered Trade Marks, manufactured respectively by Shell, Rohm and Haas and ICI) and a polyoxyethylene (12) tridecyl ether detergent as known Renex 30 (Registered Trade Mark, manufactured by Honeywell Atlas Limited). Detergent is added to a final concentration of between 0.01% and 5% v/v.

Monoclonal antibodies for use in the methods may be prepared by any method known in the art for their production (see for example Milstein, Scientific American 1980, 243 (4), 56–64). In such a method a mouse is immunised against the parasite concerned, in this case a malaria parasite for example by infection with a rodent malaria parasite. Lymphocytes, each of which will have the independent capacity to make an antibody that recognises a different antigenic determinant, are then isolated and fused with mouse myeloma cells to provide a "hybridoma". Each hybridoma will be capable of expressing the antibody of its parent lymphocyte and of being cloned. Screening of individual hybridomas provides one or more cell lines expressing the antibody, a monoclonal antibody, specific for the antigenic determinant of interest and the cell-line then used to generate large quantities of the monoclonal antibody which may then be used to separate and purify the antigenic determinant of interest. Antibodies specific for the antigens defined herein may be readily identified by simple, well known testing procedures.

The monoclonal antibody is suitably bonded to an inert support material, for example Sepharose (Trade Mark), and the solubilised material passed through the support containing antibody. This may conveniently be effected by means of a column.

The antigenic protein may be recovered from the antibody-antigen complex by disruption of the complex. The conditions for effecting this are well known in the art. Suitable conditions which preserve the immunogenicity of the protein include washing with diethylamine at high pH, for example pH 11.5 in the presence of a suitable detergent.

The antigens described above may be incorporated into a vaccine for inducing immunity to Malaria in susceptible veterbrate hosts at risk of becoming infected by parasites of the genus Plasmodium. For this purpose the antigenic proteins may be presented in association with a pharmaceutically acceptable carrier. The antigenic proteins may be used singly or in combination with other functional derivatives thereof or with other proteins which will provide protection against malaria.

In a further aspect there is provided a vaccine for inducing immunity to Malaria which comprises an antigen as hereinbefore defined or a functional derivative thereof in association with a pharmaceutically acceptable carrier.

Pharmaceutically acceptable carriers, in this instance, are liquid media suitable for use as vehicles to introduce the antigen into the patient. An example of such a carrier is saline solution. The antigenic protein may be in solution or suspended as a solid in the carrier, or it may be solubilised by the addition of pharmaceutically acceptable detergent.

The vaccine may also comprise an adjuvant for stimulating the immune response and thereby enhancing the effect of the vaccine. Convenient adjuvants for use in the present invention include Freunds complete adjuvant and more particularly, saponin, *Corynebacterium parvum* (coparvax) and aluminium hydroxide or a mixture of these or other known adjuvants.

Conveniently the vaccines are formulated to contain a final concentration of antigenic protein in the range of from 0.2 to 5 mg/ml, preferably 0.5 to 2 mg/ml, most preferably 1 mg/ml. After formulation the vaccine may be incorporated into a sterile container which is then sealed and stored at a low temperature, for example 4° C., or may be freeze dried.

In order to induce immunity in veterbrate hosts to malaria one or more doses of the vaccine suitably formulated may be administered. It is recommended that each dose is 0.1 to 2 ml preferably 0.2 to 1 ml, most preferably 0.5 ml of vaccine.

There is in a further aspect provided a method for inducing immunity to malaria in susceptible veterbrate hosts, comprising the administration of an effective amount of a vaccine, as hereinbefore defined, to the host.

The vaccines may be administered by any conventional method for the administration of vaccines including oral and parenteral (eg. subcutaneous or intramuscular) injection. The treatment may consist of a single dose of vaccine or a plurality of doses over a period of time.

Figure 1:
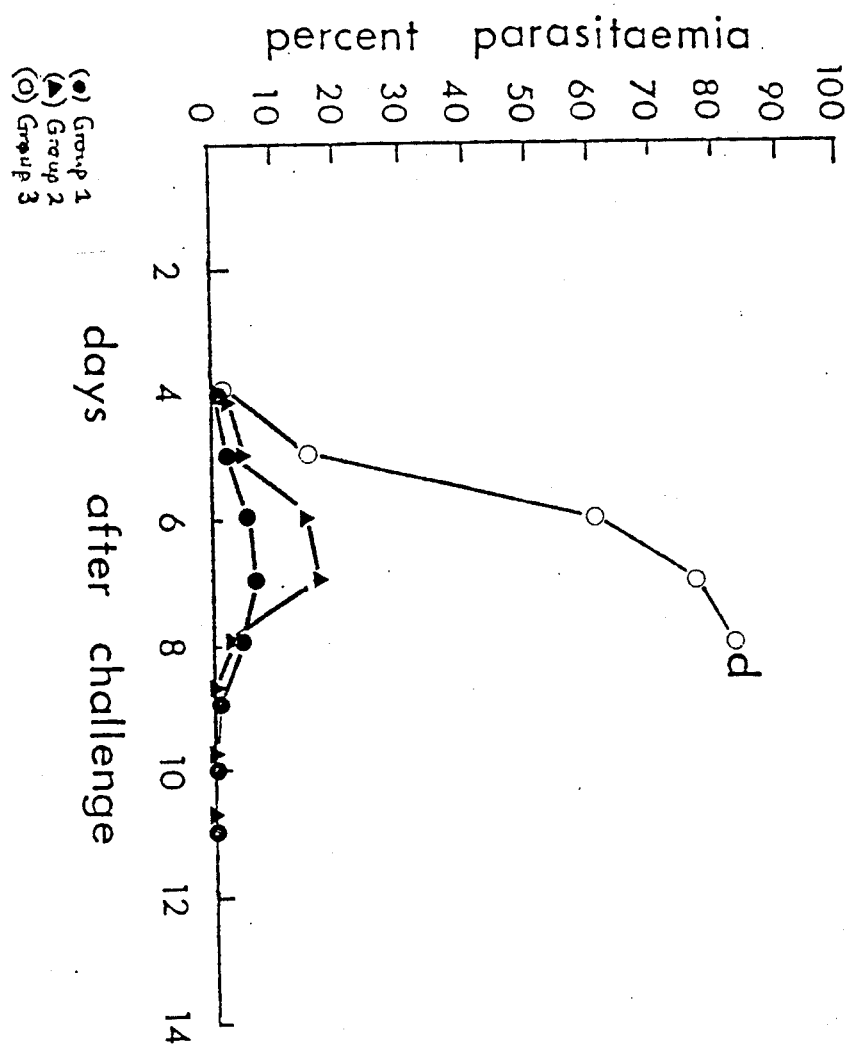
FIG. 1 shows the protection afforded mice by immunisation with antigen according to the invention, wherein 'd' indicates death, 'O' indicates the control (no immunisation), and '■' and '▲' represent immunised mice.

The following Examples serve to illustrate the invention but are not intended to limit it in any way.

EXAMPLE 1

Derivation of Hybridoma Line for *P. yoelii* antigen

Spleen cells from two *P. yoelli*-immune BALB/c mice were fused with P3-NS1/1-Ag4-1 myeloma cells in the presence of polyethylene glycol (by the general method of Galfre, et al., Nature, 1977, 266, 550–552). The cells were dispensed into 144 tissue culture wells in 2 ml volumes of HAT selective medium (Littlefield, Science, 1964, 145, 709–710) using RPMI 1640 medium supplemented with 10% foetal calf serum as a base. After 10 days the culture supernatants were tested for *P. yoelii*-specific antibody by indirect immunofluorescence (IIF). Of 143 cultures tested, 38 were positive. Culture number 1 contained an antibody specific for an antigen associated with schizonts but absent from ring-forms and trophozoites. A cloned hybridoma cell line was produced from this culture by growing colonies derived from single cells in semi-solid agar overlayed with medium. The cloned hybridoma line continued to secrete its unique antibody, was designated W1C 25.1. and has been deposited at the Institute Pasteur under the number I-160 on 16 July 1981. The hybridoma line was further grown as an ascites tumor in BALB/c mice, and ascitic fluid and serum from these mice contained about 10 mg/ml of the monospecific antibody. A second hydridoma line, W1C 45.1 secretes an antibody specific for the same antigen as antibody 25:1, with the difference that it appears to recognise only the antigen and fragments larger than $0.9 \times 10^5$ molecular weight.

EXAMPLE 2

Preparation of Antigen from *P. yoelii*

Blood forms of *Plasmodium yoelii* were grown in CD-1 mice to 80–90% parasitaemia and the erthrocytes were harvested and solubilised. The cells were solubilised by lysis at 4° C. in a buffer of 50 mM Tris, 5 mM ethylenediamine tetraacetate (EDTA), 1% Nonidet P40 pH 8.0 containing 1 mM phenylmethyl sulphonyl fluoride (PMSF), 0.1 mM tosyl-L-lysine chloromethyl ketone (TLCK), 5 mM ethyleneglycol-bis-(amino ethyl ether)N,N'-tetraacetate (EGTA) and 5 mM iodoacetamide to inhibit proteolytic activity. The lysed cells were centrifuged at 100,000 g and the supernatant, containing the erythrocyte soluble proteins and some membrane proteins, together with approximately 70% of the parasite proteins (as estimated from the proportion of $^{35}$S-methionine label in this fraction after an in vitro incorporation) collected.

Immunoglobulin from the ascites fluid of mice containing hybridoma line W1C 25.1 was purified by binding to Protein A-Sepharose and a single step elution at pH 3.0. The immunoglobulin fraction was coupled to cyanogen bromide activated Sepharose, using 10 mg immunoglobulin/ml swollen gel. The immunoabsorbant was extensively washed, packed into columns and equilibrated with 10 mM Tris, 1 mM EDTA, ImM EGTA, 1% NP40 pH 8.0.

The supernatant obtained as described above was passed through the immunoabsorbant equilibrated with 10 mM Tris, 1 mM EDTA, 1 mM EGTA, 1% NP40 pH 8.0 and washed through with this buffer. Non specifically bound material was removed by washing (5 column volumes) with this buffer containing 0.5M NaCl. The column was then washed with a buffer containing 10 mM Tris, 1 mM EDTA, 1 mM EGTA, 0.1% NP40 pH 8.0. Specific elution was achieved with 50 mM diethylamine, 0.1% NP40 pH 11.5.

The eluted material was subjected to a second cycle of immunoabsorbant chromatography. The specific eluate was dialysed against a buffer containing 10 mM Tris, 1 mM EDTA, 1 mM EGTA, 0.1% NP40 pH8.0. The sample was applied to the column which had been reequilibrated in this buffer, and washed through with 10 mM Tris, 1 mM EDTA, 1 mM EGTA, 0.5% sodium deoxycholate pH 8.2. The retained material was eluted with 50 mM diethylamine, 0.5% sodium deoxycholate pH 11.5. The eluate was conconentrated and dialysed to provide the antigen.

EXAMPLE 3

Biochemical Characterization of the Antigen and its proteolytic degradation fragments from *P. yoelii*

Antigen was labelled by incorporation of $^{35}$S-methionine into the protein by incubating parasitized cells for 2–3 hours in a medium containing this amino acid at high specific activity, the labelled antigenic protein was obtained by immunoprecipitation with the monoclonal antibody 25.1 and Protein A bearing *Staphylococcus aureus* cells to precipitate the immune complex. This material was subjected to SDS gel electrophoresis and the antigen behaved as species of $2.30 \times 10^5$ apparent molecular weight. In addition, a series of degradation products possessing the antigenic determinant was detected. The principle fragments had apparent molecular weights of 1.97, 1.60, 1.51, 1.26, 0.90, 0.56 and $0.28 \times 10^5$. Minor degradation products of apparent molecular weights 2.20, 2.13, 1.90, 1.80. 1.74, 1.48, 1.18, 1.12 and $1,04 \times 10^5$ were also present. The antigen purified by immunoabsorbant column chromatography described in Example 2, displayed a pattern of degradation products identical to that of the immunoprecipitated $^{35}$S-methionine labelled material.

The nature of the relationship of the polypeptides was revealed by peptide mapping of the major polypeptides and by pulse-chase labelling of *P. yoelii* schizonts. Homology between the amino acid sequences of the major polypeptides was clearly shown by two dimensional chymotryptic peptide mapping of $^{35}$-S-methionine-labelled polypeptides immunoprecipitated by antibody 25.1 and by limited proteolysis peptide mapping in SDS polyacrylamide gels of purified material which had been iodinated using $^{125}$I-iodine. *P. yoelii* schizonts were incubated for 10 minutes in the presence of high specific activity $^{35}$S-methionine which was then chased with non-radiactive methionine. At various time intervals after labelling samples were solubilised and immunoprecipitated with antibody 25.1. The label was intially incorporated into the $2.30 \times 10^5$ MW polypeptide, then during further incubation it sequentially appeared in the smaller polypeptides, with a concomitant reduction in the amount of label remaining in the 230,000 MW component. Thus the native antigen recognised by antibody 25.1 is a $2.3 \times 10^5$ molecular weight protein and the smaller polypeptides are proteolytic fragments of it, each retaining the antigenic determinant recognised by the monoclonal antibody. In vitro, degradation of the native protein commenced soon after its synthesis, and was extensive after 7 hours. The results indicate that the degradation occurred during incubation of the intact schizonts rather than after cell lysis and solubilisation.

The isoelectric point of the antigen and some of its fragments were determined using a 2-dimensional gel electrophoresis system based on that described by O'-Farrell (J. Biol. Chem. 250: 4007-4021, 1975) but using either a polyacrylamide or a mixed agarose/polyacrylamide gel in the first dimension. When the pH gradient was generated using pH 3-10 ampholines, the antigen and its fragments had the following approximate isoelectric points; $2.3 \times 10^5$ MW, pH 5.3-5.7; $1.6 \times 10^5$ MW, 5.2-5.5; $1.5 \times 10^5$ MW, 5.2-5.5; $0.9 \times 10^5$ MW, 6.0-6.7; $0.56 \times 10^5$, 5.2-5.4 and $0.30 \times 10^5$ MW, 5.0-5.3. The arrangement of the fragments according to isoelectric point was always $0.28 < 0.56 < 1.5$, $1.6 < 2.3 < 0.9 \times 10^5$ MW.

Standard test employing periodic acid-Schiffs staining and $^{125}$I-iodinated Concanavalin A lectin binding to the protein in polyacrylamide gels both suggested that the protein was not glycosylated.

The lack of glycosylation was confirmed by inability to specifically bind the elute the protein from lentil lectin-Sepharose and wheatgerm agglutinin-Sepharose, and by the absence of any effect on the size of the protein when synthesized by the parasite in the presence of tunicamycin, a specific inhibitor of protein N-glycosylation.

EXAMPLE 4

Localisation of the antigen associated with *P. yoelii*

By IIF using acetone-fixed cells the antigenic protein was localised to the membrane of schizonts and merozoites. Neither antibody 25.1 nor poly-valent antiserum raised against the purified protein reacted with the surface of unfixed intact schizonts in suspension. The protein was not labelled by lactoperoxidase catalysed iodination of intact schizonts, but was labelled by this technique when the cells were first solubilised by addition of 0.01% (v/v) Nonidet P 40. Furthermore the addition of trypsin (at 5 ug/ml) to the medium did not modify the processing of the protein observed during the in vitro incubation of parasitised cells, described in Example 3. It is thus considered that the proteins is not exposed on the outer surface of the host cell membrane nor localised at the inner surface of this membrane. The IIF pattern produced by antibody 25.1 suggests that the $2.30 \times 10^5$ MW protein of Example 2 is associated specifically with the plasma membrane of the developing intracellular parasite, rather than with the membrane of the host erythrocyte. This interpretation is supported by further evidence provided using a double labelling immunofluorescence technique in which acetone fixed schizonts were incubated with a mixture of antibody 25.1 (a mouse immunoglobin) and rabbit anti-mouse red cell antiserum. The slides were washed then incubated sequentially with rhodamine-conjugated goat anti-rabbit IgG antiserum and with FITC-conjugated rabbit anti-mouse IgG antiserum. Upon examination it was noted that the *P. yoelii* schizont antigen (traced with FITC) was localised at a membrane distinct from, and enclosed within, the host red cell membrane (traced with rhodamine).

In early schizonts, prior to the formation of the residual body, the antigen appears to be localised at a spherical membrane enclosing the parasite, but the following segmentation and formation of the residual body, the membrane appears to surround individual merozoites. Thus the $2.3 \times 10^5$ MW protein (and/or proteolytic derivatives of it) is evenly distributed on free merozoites as well as being associated with schizonts.

In the IIF test with free merozoites in suspension, antibody 25.1 gave a positive florescense indicating that the antigen is on the surface of the merozoites.

EXAMPLE 5

Immunisation of mice with an antigen of *Plasmodium yoelli*, purified using monoclonalantibody 25.1: antibody response Groups of 5 BALB/c mice were immunised with the antigenic protein obtained from Example 2 or with control preparations according to the following schedule:

Group 1:
  50μg antigen 25.1 emulsified in Freund's Complete Adjuvant (FCA) and injected intraperitoneally (i.p.) in a volume of 0.2 ml on day 0.
  20 μg antigen 25.1 suspended in 0.2 mls normal mouse serum and injected intravenously on day 26.
  25 μg antigen 25.1 suspended in saline and injected i.v. on day 39.

Group 2:
  FCA only, given i.p. day 0
  NMS only, given i.v. on day 18
  Saline only, given i.v. on day 42.

On day 49, serum samples were taken for titration and examination by indirect immunofluorescence (IIF). The results are shown below.

| Group | Mouse | IIF titre | antiserum specificity |
|---|---|---|---|
| 1 | 1> | 1:5120 | schizonts and merozoites |
|   | 2> | 1:5120 | schizonts and merozoites |
|   | 3> | 1:5120 | schizonts and merozoites |
|   | 4> | 1:5120 | schizonts and merozoites |
|   | 5> | 1:640  | schizonts and merozoites |
| 2 | 1< | 1:40 | — |
|   | 2< | 1:40 | — |
| " | 3< | 1:40 | — |
|   | 4< | 1:40 | — |
|   | 5< | 1:40 | — |

The pattern of fluorescent staining using the serum from the mice immunised with antigen 25.1 was indistinguishable from that produced using monoclonal antibody 25.1. Staining was restricted to the schizont and merozoite forms of *P. yoelli*. This result confirmed the purity and immunogenic nature of antigen 25.1 prepared as described in Example 2.

EXAMPLE 6

Immunisation of mice with an antigen of *Plasmodium yoelii*, purified using monoclonal antibody 25.1: protection against challenge infection Groups of 5 BALB/c mice were immunised with the antigenic protein obtained from Example 2, or with control preparations according to the following schedule:

Group 1:
  12 μg antigen 25.1 emulsified in FCA and injected i.p. in a volume of 0.2 mls on day 0.
  12 μg antigen 25.1 in FCA i.p. on day 35.
  20 μg antigen 25.1 in 0.1 ml saline i.v. on day 50.

Group 2:
  2 μg antigen 25.1 in FCA i.p. on day 0.
  2 μg antigen 25.1 in FCA i.p. on day 35.
  20 μg antigen 25.1 in 0.1 ml saline i.v. on day 50.

Group 3:
Saline in FCA i.p. on day 0.
Saline in FCA i.p. on day 35.
0.1 ml saline given i.v. on day 50.

On day 60, serum samples were taken for IIF titration of antibody, and for analysis by immunoprecipitation. On day 61 all mice were challenged i.v. with $10^4$ P. yoelii YM-parasitised erythrocytes. The antibody response of the groups on immunised mice are given in Table 1. The results demonstrate that under the conditions used, immunisation with 12 μg of antigen 25.1 was more effective in inducing an antibody response than was immunisation with 2 μg of antigen 25.1.

TABLE 1

Antibody response of mice immunised with antigen 25.1

| Group | IIF titre | antiserum specificity |
|---|---|---|
| 1 | >1:10240 | schizonts and merozoites |
| 2 | >1:5120 | schizonts and merozoites |
| 3 | <1:40 | nonspecific |

The protection against challenge with P. yoelii provided to each group shown in FIG. 1. The results show that the group with the higher antibody titre were more effectively protected against challenge. The control group of mice all died within 8 days of challenge. All mice immunised with antigen 25.1 survived.

The antigenic specificity of serum from the immunised mice was checked by immunoprecipitation which demonstrated that the antibody response was directed against the 230,000 m.w. schizont antigen (and its degradation fragments) used for immunisation.

EXAMPLE 7

Identification of the Antigen from P. falciparum

A schizont-enriched fraction of erythrocytes, parasitised with P. falciparum prepared by centrifugation through a layer of Percoll, was labelled with $^{35}$S-methionine during a period of 2 hours. The cells were harvested and solubilised by lysis at 4° as described in Example 2. After centrifugation the supernatant was used for immunoprecipitateion with an antibody specific for P. falciparum and derived from a hybridoma prepared by the method of Example 1. The specific precipitate was subjected to SDS gel electrophoresis and the antigen behaved as a species of $1.95 \times 10^5$ apparent molecular weight. In addition, a number of discrete degradation products were observed. The principle fragments had molecular weights of 1.53, 1.50 and $0.83 \times 10^5$ and additional minor fragmens of 1.12, 1.10 and $1.08 \times 10^5$ molecular weight were also present.

The identification of the $1.95 \times 10^5$ molecular weight component as the primary protein, from which the specific fragments were subsequently derived, was confirmed by labelling the cells for a short period of 20 minutes. Immunoprecipitates from extracts of this material using the P. falciparum antibody contained all of the $^{35}$S-methionine label in the $1.95 \times 10^5$ molecular weight antigen.

This antigen (and its specific fragments) is strongly represented in the material recognised by human immune serum to P. falciparum as assessed by immunoprecipitation and SDS gel electrophoresis.

The amino acid sequence relatedness of the major fragments and the $1.95 \times 10^5$ M.W. species was confirmed by peptide mapping of the $^{35}$S-methionine-containing peptides. The isoelectric points of the antigenand its fragments were determined as approximately 5.8($1.95 \times 10^5$), 5.2(1.53 and $1.50 \times 10^5$), 6.0($1.10 \times 10 \times 10^5$), and 6.1-6.5($0.83 \times 10^5$).

EXAMPLE 8

Preparation of Antigen from P. falciparum

P. falciparum parasites grown in culture in human erythrocytes, were harvested and solubilised, as described in Example 2. The solubilised material was passed down a column of Sepharose coupled with immunoglobulin obtained from the ascites fluid of mice containing hybridoma line W1C 89.1. When the column was washed and eluted with 50 mM diethylamine, 0.1% NP4O, pH 11.5, as described in Example 2 the eluate contained predominantly the $1.95 \times 10^5$ MW antigen and the $0.83 \times 10^5$ MW fragment.

EXAMPLE 9

Synthesis and processing of the antigen from P. falciparum

The synthesis and processing of the protein during the intracellular development of the parasite was investigated during one 48 hour cycle in an in vitro culture of P. falciparum which had been synchronised by two treatments with sorbitol 33 hours apart. The stage of development was monitored by morphological examination of Giemsa stained parasites, every 3 hours after the second sorbitol treatment. Only ring forms were observed for the first 12 hours, after which time trophozoites begun to appear and were present maximally at 24 hours. Schizonts were first observed at 27 hours and predominated at 39 hours. At 39 hous a small number of new ring forms were visible, indicating that some merozoite release had occured, although most ring forms did not appear until 45–48 hours.

At six hour intervals the polypeptides synthesised during a 30 minute pulse with $^{35}$S-methionine were investigated. Maximal protein synthesis occured during schizogeny, at 36 hours. The time of synthesis of many proteins was restricted during the development cycle. One of the abundant proteins synthesised only during schizogeny was the $1.95 \times 10^5$ MW protein.

When the proteins synthesised at each time immunoprecipitated with pooled immune human serum. A clear pattern was observed. During the ring and trophozoite stages only two polypeptides of $1.6 \times 10^5$ MW and $0.71 \times 10^5$ MW were recognised by human immune serum and precipitated. During schizogeny a number if polypeptides were recognised by human immune serum. The predominant species (larger than $0.3 \times 10^5$) had molecular weights of 0.37, 0.40, 0.46, 0.62, 0.72, 0.80, 0.84, 0.89, 1.04, 1.20, 1.34, 1.46 (doublet), 1.78, 1.95, 2.08, 2.20 and $2.35 \times 10^5$. The synthesis of several of these proteins was at specific times during schizogeny. The $1.95 \times 10^5$ MW antigen was recognised by the immune serum and was synthesised throughout schizogeny.

The monoclonal antibody 89.1 also precipitated the $1.95 \times 10^5$ MW protein throughout schizogeny. The processing of the protein subsequent to its synthesis, was investigated by performing immunoprecipitations on the solubilised pulse labelled material and also on solubilised material from cells which had been pulse labelled and then chased with unlabelled methionine for 60 or 120 min. At 30 h into the parasite development cycle (immature schizonts) the 120 min chase resulted in no apparent shift in the label to lower molecular weight bands. At 42 h most of the radioactivity was incorporated during the pulse period into the 195,000 MW band but after 60 min chase the 1.53 and $1.50 \times 10^5$ MW bands were more apparent and the $0.83 \times 10^5$ MW band appeared. After 120 min chase the $0.83 \times 10^5$ MW band increased in intensity and some of the label was associated with a $0.6 \times 10^5$ MW polypeptide. After 45 h of parasitedevelopment, processing of the 195,000 MW protein to its discrete fragments was much more extensive during the chase period. (The immunoprecipitate at 48 h showed that some processing of the 195,000 MW protein through to the 60,000 MW fragment had occurred even within the 30 minuted pulse period). The onset of processing was concomitant with the appearance of new ring forms in the culture and, therefore, also with the maturation of schizonts and release of infective merozoites.

EXAMPLE 10

Localisation of the antigen associated with *P. falciparum* and cross-reaction with a polyvalent serum raised against the *P. yoelii* antigen By IIF using acetone-fixed cells the antigenic protein was localised to the membrane of schizonts and merozoites, the distribution being identical to the antigen described in Example 4. Immunological cross-reaction between the antigen of *P. yoelii* and that of *P. falciparum* was demonstrated by raising high titre polyvalent antiserum in mice to the *P. yoelii* antigen, which had been prepared as described in Example 2. When this antiserum was assayed by immunofluorescence with *P. yoelii* infected mouse cells, the pattern of fluorescent staining was indistinguishable from that produced using monoclonal antibody 25.1 and the antiserum had a titre of 1 in 20,000. When this antiserum was assayed against *P. falciparum* infected human red cells, it gave a staining pattern identical to that of antibody 89.1, with an IIF titre of 1 in 1,600. This indicates an immunological cross-reaction between the two antigens which is probably related to their structural similarities.

EXAMPLE 11

Vaccines

Vaccines for use in immunisation may be prepared by conventional techniques with the following constituents:

| Formulation A | |
|---|---|
| Antigen | 2 mg |
| Physiological Saline to | 1 ml |
| Formulation B | |
| Antigen | 1 mg |
| Alhydrogel | 1 mg |
| Physiological Saline to | 1 ml |

We claim:
1. An protection-inducing proteinaceous antigen of a parasite of the species *Plasmodium yoelii* and *Plasmodium falciparum* characterized by an apparent molecular weight in the range of $1.8 \times 10^5$ to $2.5 \times 10^5$; and in the case of *Plasmodium yoelii* an approximate isoelectric point of 5.3–5.7 and in the case of *Plasmodium falciparum* an approximate isoelectric point of 5.8; the antigen in its native state being associated with the membrane of the erythrocytic schizont form of the parasite and being processed intraerythrocytically to discrete fragments possessing the same antigenic properties, the resulting processed antigen being associated with the membrane of the merozoite form of the parasite; or a protection-inducing functional derivative thereof.

2. An antigen as claimed in claim 1, wherein the apparent molecular weight is from $1.9 \times 10^5$ to $2.3 \times 10^5$.

3. An antigen as claimed in claim 2, wherein the apparent molecular weight is about $1.95 \times 10^5$.

4. An antigen as claimed in claim 3, which in its native state is processed intraerythrocytically to discrete fragments having apparent molecular weights of $1.53 \times 10^5$ and $1.50 \times 10^5$, and isoelectric points of 5.2 and 6.2–6.5 respectively.

5. A protection-inducing fragment of an antigen of *Plasmodium falciparum*, as defined in claim 1, the fragment having an apparent molecular weight of $1.53 \times 10^5$ and an isoelectric point of 5.2.

6. A protection-inducing fragment of an antigen of *Plasmodium falciparum*, as defined in claim 1, the fragment having an apparent molecular weight of $1.50 \times 10^5$ and an isoelectric point of 5.2.

7. A protection-inducing fragment of an antigen of *Plasmodium falciparum*, as defined in claim 1, the fragment having an apparent molecular weight of $0.83 \times 10^5$ and an isoelectric point of 6.5.

8. A process for preparing an antigen, as claimed in claim 1, which comprises the steps of:
(i) solubilising erythrocytes containing the schizont form of the parasite;
(ii) contacting the solubilised materials with a monoclonal antibody specific for the desired antigen to provide an antibody-antigen complex; and
(iii) recovering the antigen from the antibody-antigen complex.

9. A vaccine for inducing immunity to malaria in a susceptible vertabrate host which comprises an effective amount of an antigen or fragment as defined in claims 1, 2, 3, 4, 5, 6 or 7 together with a pharmaceutically acceptable carrier therefor.

10. A method for inducing immunity against malaria in a vertabrate host which comprises injecting into said vertabrate host a vaccine of claim 9.

* * * * *